United States Patent
Furuya et al.

[11] 4,089,606
[45] May 16, 1978

[54] ECHINATIN GLYCOSIDES

[75] Inventors: Tsutomu Furuya, Tokyo; Shinichi Ayabe, Tokosuka; Miyuki Kobayashi, Ube; Tadao Tanimoto, Okayama, all of Japan

[73] Assignee: Kabushiki Kaisha Hayashibara Seibutsu Kagaku Kenkyujo, Okayama, Japan

[21] Appl. No.: 672,623

[22] Filed: Apr. 1, 1976

[30] Foreign Application Priority Data

Apr. 17, 1975 Japan .................................. 50-47240
Apr. 17, 1975 Japan .................................. 50-47241

[51] Int. Cl.² .................................. C07H 15/20
[52] U.S. Cl. .................................. 536/4; 195/31 R; 195/31 P; 424/180; 424/181; 536/5
[58] Field of Search .................................. 536/4, 8

[56] References Cited

U.S. PATENT DOCUMENTS

3,876,777  4/1975  Horowitz et al. .................. 536/8
3,960,835  6/1976  Robertson .................. 536/4

OTHER PUBLICATIONS

Noller "Chemistry of Organic Compounds" 3rd Ed., 1965, W. B. Sanders Co., Phila., Pa. pp. 583 and 872.

*Primary Examiner*—Johnnie R. Brown
*Attorney, Agent, or Firm*—Browdy and Neimark

[57] ABSTRACT

Echinatin glycosides are disclosed having the following formula

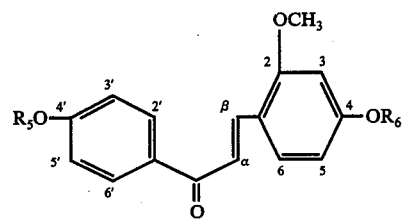

wherein $R_5$ and/or $R_6$ is a glycosyl residue. These substances have pharmacological effects such as the inhibiting action of the echinatin-4'-glucoside on the growth of human lymphoblastoids. These compounds may be chemically synthesized by subjecting a compound of the following formula

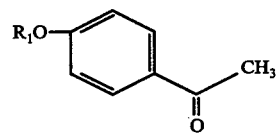

to reaction with a compound represented by the following formula

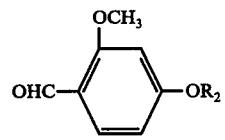

in which $R_1$ and/or $R_2$ is a glycosyl residue or an acyl glycosyl residue, with the optional successive step of subjecting the resultant to reaction with a glycosyl halide or an acyl glycosyl halide.

1 Claim, 1 Drawing Figure

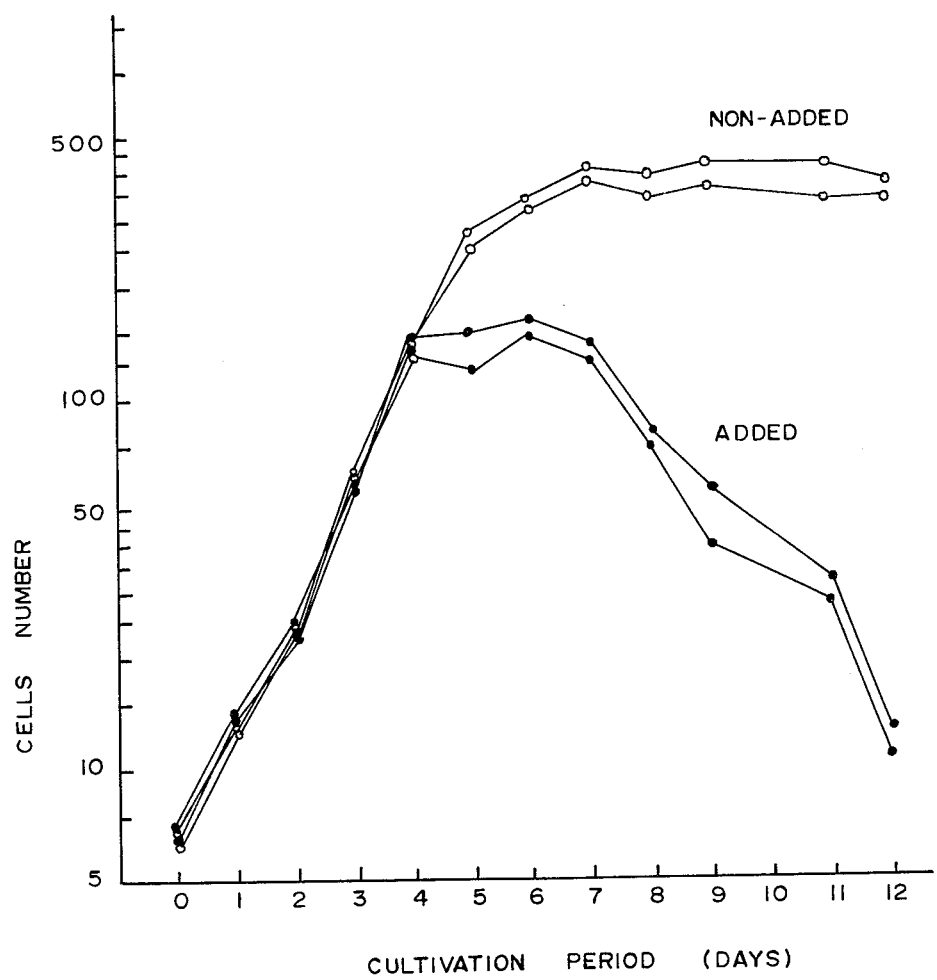

ECHINATIN GLYCOSIDES

DETAILED DESCRIPTION OF THE PRESENT INVENTION

The present invention relates to echinatin glycosides represented in Formula (V),

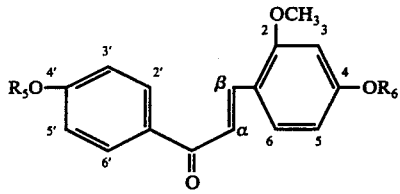

Formula (V)

(wherein $R_5$ and/or $R_6$ is a glycosyl residue and the remainder, if any, is a hydrogen residue) and processes for their production.

Echinatin, reported by Furuya et al. (Tetrahedron Letters No. 27,2567 (1971)) as existing in tissue cultures of *Glycyrrhiza echinata* L. (Leguminosae), is a promising substance with potential pharmacological efficacies.

Industrial utilization of echinatin in its intact form was so far difficult due to its extremely low water solubility.

The echinatin glycosides which the present inventors succeeded in producing after years of research and development are very readily water soluble in comparison with echinatin and are novel substances which have pharmacological effects such as the inhibiting action of echinatin-4'-glucoside on the growth of human lymphoblastoid.

The echinatin glycosides represented in Formula (V) can be prepared by one of the following methods; (a) a chemical synthesis characterized by subjecting the compound represented in Formula (I)

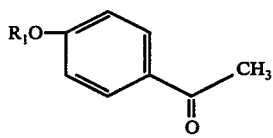

Formula (I)

to reaction with the compound represented in Formula (II)

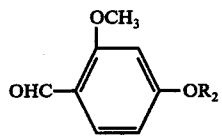

Formula (II)

(in Formulae (I) and (II) $R_1$ and/or $R_2$ is a glycosyl residue or an acyl glycosyl residue, and the remainder, if any, is a hydrogen atom), (b) a chemical synthesis characterized by subjecting the compound represented in Formula (III)

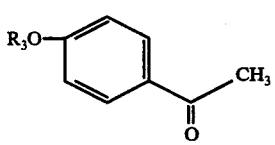

Formula (III)

to reaction with the compound represented in Formula (IV)

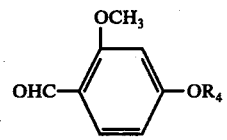

Formula (IV)

(in Formulae (III) and (IV) $R_3$ and/or $R_4$ is a hydrogen atom and the remainder, if any, is a glycosyl residue or an acyl glycosyl residue) and successively subjecting the resultant to reaction with a glycosylhalide or an acyl glycosylhalide, or (c) a biosynthesis characterized by cultivating calli of *Glycyrrhiza echinata* L. (Leguminosae) in a nutrient medium to form echinatin glycosides in the calli and culture broth.

The processes will be illustrated in detail, starting with the chemical syntheses. The reaction between the compounds of Formulae (I) and (II) and that between those of Formulae (III) and (IV) are carried out by dissolving the compounds in an organic solvent such as methanol, ethanol and acetone, adding thereto an alkali hydroxide, such as sodium hydroxide and potassium hydroxide, and then allowing reaction of the mixture at a temperature not higher than 40° C with continuous stirring.

In reacting the chemical product obtained by the reaction between compounds of Formulae (III) and (IV) with a glycosylhalide or an acylglycosylhalide, the product and the halides are dissolved similarly as above in an organic solvent such as methanol, ethanol, acetone, added alkali hydroxide, such as sodium hydroxide and potassium hydroxide, and allowed reaction at a temperature not higher than 40° C with continuous stirring. Further, if deacylation of the reaction mixture is desirable, the treatment can be carried out by any usual method, such as that with an alkali hydroxide.

The compound given in Formula (V) is prepared by removing the echinatin glycosides from the reaction mixture by neutralization of the reaction mixture, solvent extraction or column chromatography, and then purifying the resultant, if necessary, by desalting with ion exchangers or by repetition of crystallization.

In the production of the compounds of Formulae (I) and (III), the starting material is, for example, 4-hydroxyacetophenone, while for the compounds of Formulae (II) and (IV) it is, for example, 2-methoxy-4-hydroxybenzaldehyde. In order to bind glycosyl residues to the compounds, the compounds are subjected to reaction with an acylglycosylhalide, for example 2,3,4,6-tetra-O-acetyl-alpha-D-glycopyranosyl bromide. Various sugars, for example, ribofuranose, glycopyranose, mannopyranose, galactopyranose, maltose, lactose and cellobiose, can be used as the glycosyl residues represented by $R_1$, $R_2$, $R_3$, $R_4$, $R_5$ and $R_6$.

The compound represented by Formula (V) is an echinatin-4'-glycoside when $R_5$ is a glycosyl residue and an echinatin-4-glycoside when $R_6$ is a glycosyl residue, while it is an echinatin-4, 4'-diglycoside when $R_5$ and $R_6$ are both glycosyl residues.

Furthermore the two glycosyl residues of echinatin diglycosides may be identical or different.

The biosynthesis is a process where calli of *Glycyrrhiza echinata* L. (Leguminosae) are cultivated on a nutrient medium to form echinatin glycosides in the calli and culture broth. More particularly, the calli are obtained by cultivating cells or tissues taken from one or more members selected from a group comprising radicles, hypocotyls, cotyledons and plumules of young plant, and roots, stems, leaves and flowers of matured plant of *Glycyrrhiza echinata* L. (Leguminosae) on a nutrient medium to which auxins, sugars and vitamins are added.

The auxins may be, for example, 2,4-dichlorophenoxy-acetic acid, naphthalene-1-acetic acid, indole-3-acetic acid, indole-3-propionic acid and kinetin; sugar, for example, monosaccharides such as glucose, galactose, sorbitol and glycerol, disaccharides such as maltose and sucrose, or oligosaccharides such as dextrins; vitamins, for example, myoinositol, thiamine-HCl, nicotinic acid and pyridoxine-HCl; and, if necessary, amino acids, for example glycine and sodium monoglutamate, are also employable.

Cultivation is carried out on a well-known medium, for example the Murashige-Skoog's medium and the White's medium to which are added the above mentioned auxins and vitamins. However, a nutrient medium, to which, at least, one member of a group comprising naturally-occurring substances, for example, yeast, chlorella, chrysalis, bonito, malt, tomato and soybean, their products, for example, casein hydrolysate, peptone, fish soluble, corn steep liquor, coconut milk, and their extracts, is or are added, is preferable. The temperature range for the cultivation is from 20° to 34° C, preferably from 24° to 30° C.

The cultivation is accomplishable within a period of 1 to 10 weeks by either static or aeration-agitation culture, in light or in darkness.

Since not only echinatin glycosides are generally formed in the calli obtained by the above-mentioned cultivation but also echinatins, the echinatin glycosides may be, if necessary, extracted with water or organic solvent, then separated, purified by chromatography or repetition of crystallization, and collected. In the case of liquid culture, generally, echinatin glycosides can be also accumulated in the culture broth as well as in the calli.

The water solubility of echinatin glycosides, at 15° C, is several thousand times higher than that of echinatin which is less than 0.0001%. For example, the respective water solubilities of echinatin-4'-glycoside, echinatin-4-glucoside and echinatin-4,4'-diglucoside are about 1%, 0.1% and 0.5%. The water solubilities of the echinatin glycosides prepared according to the present invention are freely adjustable by treatment with glycosidase or transglycosidase.

The invention will now be further described with reference to the following examples in which all parts or percentages are by weight unless specified otherwise.

EXAMPLE 1

(A)
1,2,3,4,6-penta-O-acetyl-beta-D-glucopyranose—Compound (VI)

After maintaining a mixture, prepared by adding 50 parts sodium acetate anhydride and 500 parts acetic anhydride to 100 parts glucose at 100° C, in an oil bath at 5° C for four hours, the resultant was poured into 4000 parts ice water while constantly stirring, and the formed precipitates were filtered off and washed with water until the filtrate became chemically neutral. Three repetitions of crystallization of the precipitates yielded 95 parts 1,2,3,4,6-penta-O-acetyl-beta-D-glucopyranose, hereinafter referred to as Compound (VI), with a melting point of 129° C.

(B) 2,3,4,6-tetra-O-acetyl-alpha-D-glucopyranosyl bromide—Compound (VII)

A mixture prepared by adding 30 parts red phosphorus to 300 parts glacial acetic acid was cooled in an ice-water bath, and after gradual addition of 180 parts bromine the resultant was filtered to collect the filtrate.

After adding 32.7 parts of Compound (VI) to 70 parts of the filtrate, the mixture was subjected to reaction for four hours. Following addition of 100 parts chloroform and sufficient stirring, the mixture was poured into 200 parts ice water and subsequently the chloroform layer was recovered with a separating funnel. The layer was water-washed until it became chemically neutral, then calcium chloride was added, it was dried thoroughly and concentrated. Two repetitions of crystallization of the concentrate from isopropyl ether yielded 28.5 parts crystalline 2,3,4,6-tetra-O-acetyl-alpha-D-glucoypranosyl bromide, hereinafter referred to as Compound (VII), with a melting point of 89° C.

(C)
4-O-2',3',4',6'-tetra-O-acetyl-alpha-D-glucopyranosyl acetophenone—Compound (VIII)

After cooling in an ice bath, a mixture prepared by dissolving 3.4 parts 4-hydroxyacetophenone and 10 parts Compound (VII) in 22 parts acetone has added thereto gradually, 11 parts of 9% sodium hydroxide and it is stirred for 45 minutes, whereupon to the mixture was added gradually 22 parts acetone with constant stirring and then the resulting mixture was subjected to reaction for 14 hours. Then the reaction mixture was concentrated under reduced pressure and at a temperature not higher than 30° C, and the concentrate was washed six times with about 150-part portions of water. Successively, the resultant was crystallized thrice from a methanol-water system solvent to yield 3.2 parts 4-O-2',3',4',6'-tetra-O-acetyl-alpha-D-glucopyranosyl acetophenone, hereinafter referred to as Compound (VIII), which had a melting point of 172° C.

(D) 2-methoxy-4-hydroxybenzaldehyde—Compound (IX)

To 20 parts 2-methoxyophenol and 50 parts zinc cyanide, which were conditioned to an absolutely anhydrous state in a three-neck flask, was added 200 parts anhydrous ethylether. While blowing anhydrous chloride gas into the mixture 30 parts aluminum chloride was simultaneously added, and the resultant was subjected to reaction for 4 hours to form a viscous oily matter. To the oily matter obtained from the reaction mixture by decantation was added water, it was cooled and the formed precipitates were separated and recovered. The precipitates were crystallized from water, thereafter thrice from a methanol-water system solvent to yield 10.2 parts 2-methoxy-4-hydroxybenzaldehyde, hereinafter referred to as Compound (IX), which had a melting point of 151° C.

(E)
2-methoxy-4-O-2',3',4',6'-tetra-O-acetyl-glycopyranosyl benzaldehyde—Compound (X)

3.7 Parts of Compound (IX) and 10 parts of Compound (VII) were dissolved in 22 parts acetone. To the mixture was added gradually 11 parts of a 9% aqueous sodium hydroxide solution with cooling and constant stirring, and then the resultant was subjected to reaction for 45 minutes. Thereafter, 22 parts acetone was added to the reaction mixture and it was subjected to reaction for additional 14 hours with constant stirring. After concentration under reduced pressure, the concentrate was washed six times with about 150 part portions of water and successively crystallized thrice with an ethanol-water solvent system to yield 5.2 parts crystalline 2-methoxy-4-O-2′,3′,4′,6′-tetra-O-acetyl-glucopyranosyl benzaldehyde, hereinafter referred to as Compound (X), which had a melting point of 127° C.

(F) Echinatin-4′-glucoside 3.0 Parts of Compound (VIII) was dissolved in 5.0 parts of a 90% aqueous ethanol solution and to the mixture was added 15 parts of 60% potassium hydroxide while cooling the mixture in an ice bath and maintaining constant and thorough stirring for 5 minutes, whereupon to the resulting mixture was added 1.0 part of Compound (IX) and 6 parts of a 60% aqueous potassium hydroxide solution, and the resultant was subjected to reaction with constant stirring and cooling for 48 hours. On completion of the reaction, the resultant was diluted to two-times volume with water and neutralized with an approximately 10% aqueous solution of hydrogen chloride to between neutral and faintly acidic to form yellow precipitates. The precipitates were filtered off, and fractionated by silica-gel column chromatography using a chloroform-methanol (7:3) system developer. The yellow-zone fractionates thus obtained were concentrated and then crystallized from ethylacetate to yield 0.5 parts of yellow needle-crystalline echinatin-4′-glucoside which is a product represented by Formula (V).

Properties of the product were as follows: melting point: 163°–165° C (decomp.); elemental analysis: molecular formula $C_{22}H_{24}O_9$ = 432.431, theoretical value C=61.11%, H=5.59%, whereas experimental values were C=59.85%, H=5.84%;
IR $\nu_{max}^{KBr}$ Cm$^{-1}$: 3380 (OH), 1638 (alpha-beta unsaturated C=O);
UV $\lambda_{max}^{MeOH}$ nm (log ξ): 373 (4.37), 305 (4.06);
UV $\lambda_{max}^{MeOH-NaOCH_3}$ nm (log ξ): 435 (4.51), 278 (4.12);
NMR (d$_6$-DMSO/D$_2$O, 100 MHz) δ (ppm): 3.2–3.6 (6H, glucose, $\underline{H}$—C—OH,

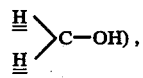

3.6–3.8 (5H, glucose, C—OH), 3.91 (3H, S, (2), OCH$_3$), 4.99 (1H, d, J=7.0, glucose, (1) β), 6.33 (1H, d, J=1.5, (5)), 6.38 (1H, d, J=8.0, (3)), 7.07 (2H, d, J=7.9, (3′,5′), 7.56 (1H, d, J=16, (α)), 7.69 (1H, d, J=8.3, (6)), 7.89 (1H, d, J=15.6, (β)), 8.00 (2H, d, J=8.4, (2,6)), 10.10 (1H, (4) OH).

The product, in aqueous solution form, was neutral, had a water solubility (15° C) of approximately 1%, and its thin layer chromatogram (TLC) obtained by using a chloroform-methanol (7:3) system developer showed an Rf of about 0.5. When the TLC was exposed to ultra violet ray (365 nm) the echinatin-4′-glucoside spot displayed green fluorescence. The product became brilliantly yellow with 2N sodium hydroxide, and orange with 2N sulfuric acid, and orangish brown when heated to 110° C.

EXAMPLE 2

Similarly, 0.55 parts of Compound (X) and 0.15 parts 4-hydroxyacetophenone were reacted and the resultant was purified as in the echinatin-4′-glucoside process which was described in Example 1 (F) to yield 0.35 parts of yellow needle-crystalline echinatin-4-glucoside which is another product represented by Formula (V).

The properties of the product were as follows: melting point, 200°–202° C (decomp.); elemental analysis: molecular formula $C_{22}H_{24}O_9$=432.431; theoretical value C=61.11%, H=5.59%, whereas experimental values were C=59.60%, H=5.74%;
IR $\nu_{max}^{KBr}$ Cm$^{-1}$: 3360 (OH), 1640 (alpha-beta unsaturated C=O);
UV $\lambda_{max}^{MeOH}$ nm (log δ): 358 (4.40), 250 (4.20);
UV $\lambda_{max}^{MeOH-NaOCH_3}$ nm (log ξ): 385 (4.46), 300 (4.00);
NMR (d$_6$-DMSO/D$_2$O, 100 MHz) δ (ppm): 3.2–3.6 (6H, glucose, $\underline{H}$—C—OH,

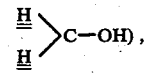

3.6–3.8 (5H, glucose, C—OH), 3.84 (3H, S, (2), OCH$_3$), 4.87 (1H, d, J=8.1, glucose, (1) β), 6.62 (1H, d, J=1.5, (3)), 6.67 (1H, d, J=8.1, (5)), 6.85 (2H, d, J=8.0, (3′,5′)), 7.65 (1H, d, J=16.2, (α)), 7.80 (1H, d, J=8.0, (6)), 7.96 (1H, d, J=16.1, (β)), 7.97 (1H, d, J=8.2, (2,6)), 10.20 (1H, 4′, OH).

The product in aqueous solution form was neutral, its water solubility (15° C) was about 0.1%, and its TLC had an Rf value of about 0.5 when developed with a chloroform-methanol (7:3) system. The echinatin-4-glucoside spot on the TLC displayed a green fluorescence when exposed to ultra violet ray, 365 nm. The product because yellow with 2N sodium hydroxide, orange with 2N sulfuric acid, and orangish brown when heated to 110° C.

EXAMPLE 3

Similarly as in Example 1 (F), 0.5 parts of Compound (VIII) and 0.5 parts of Compound (X) were subjected to reaction, neutralized, fractionated by silica-gel column chromatography, and concentrated under reduced pressure to yield 0.38 parts powdered, yellow-tinted echinatin-4,4′-diglucoside, which is another product represented by Formula (V).

The properties of the product were as follows: melting point; 159°–161° C (decomp.);
IR $\nu_{max}^{KBr}$ Cm$^{-1}$: 3360 (OH), 1640 (alpha-beta unsaturated C=O);
UV $\lambda_{max}^{MeOH}$ nm (log ξ): 360 (4.80), 308 (4.53), 250 (4.48);
UV $\lambda_{max}^{MeOH-NaOCH_3}$ nm (log ξ): 358 (4.70), 300 (4.55);
NMR (d$_6$-DMSO/D$_2$O, 100 MHz) δ (ppm): 3.2–3.6 (12H, glucose, $\underline{H}$—C—OH,

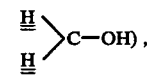

3.6–4.2 (8H, glucose, C—OH), 3.88 (3H, S, (2), OCH$_3$), 5.02 (2H, glucose, (1) β), 6.68 (1H, d, J=8.0, (5)), 6.74 (1H, d, J=3.0, (3)), 7.45 (2H, d, J=8.1, (3′,5′)), 7.72 (1H, d, J=16.0, (α)), 7.85 (1H, d, J=7.9, (6)), 7.97 (1H, d, J=15.9, (β)), 8.04 (2H, d, J=8.2, (2′,6′)).

The product in aqueous solution form was neutral, its water solubility (15° C) about 0.5%, and its TLC had an Rf value of about 0.1 when developed with a chloroform-methanol (7:3) system. The echinatin-4,4'-diglucoside spot on the TLC displayed a green fluorescence when exposed to ultra violet ray, 365 nm. The product became yellow with 2N sodium hydroxide, faintly orange with 2N sulfuric acid, and from brown to dark brown when heated at 110° C.

EXAMPLE 4

0.2 Parts of the echinatin-4'-glucoside obtained in Example 1 (F) and one part of Compound (VII) obtained in Example 1 (B) were subjected to reaction similarly as in the case of Example 1 (C), deacetylated by usual method and purified similarly as in Example 3 to yield 0.1 part of faintly yellow product which showed properties identical to those of echinatin-4,4'-diglucoside which is another product represented by Formula (V).

EXAMPLE 5

Two parts of Compound (IX) obtained in Example 1 (D) and two parts of 4-hydroxyacetophenone were reacted similarly as in Example 1 (F) and purified to obtain 0.8 parts of yellow crystals with a melting point of 210°–212° C (decomp.). The resultant was allowed to react similarly as in Example 1 (C) with three parts of Compound (VII) obtained in Example 1 (B). After deacetylation reaction by usual method, the resulting mixture was fractionated by column chromatography and purified to obtain 0.1 part of echinatin-4'-glucoside which showed properties identical to those of compound of Example 1 (F), 0.1 part of echinatin-4-glucoside which showed properties identical to those of compound of Example 2, and 0.2 parts of powder echinatin-4,4'-diglucoside which showed properties identical to those of the product obtained in Example 3. The three products are those represented by Formula (V).

EXAMPLE 6

400 ml portions of modified White's medium, prepared by adding 0.1 ppm 2,4-dichlorophenoxyacetic acid, 0.1 w/v% yeast extract, 2.0 w/v% sucrose, 1.0 w/v% agar to a White's medium comprising the followings, were placed in 250 Ehrenmeyer's flasks, inoculated with plumule calli of *Glycyrrhiza echinata* L. (Leguminosae), and then the flasks were subjected to static culture in dark and at a temperature of 26° C for 6 weeks followed by separation of the calli.

| White's medium, per liter deionized water | | |
|---|---|---|
| Potassium nitrate | 80 | mg |
| Potassium chloride | 65 | mg |
| Calcium nitrate . 4H$_2$O | 300 | mg |
| Magnesium sulfate . 7H$_2$O | 720 | mg |
| Sodium sulfate | 200 | mg |
| Sodium dihydrogen phosphate . H$_2$O | 16.5 | mg |
| Ferric sulfate | 2.5 | mg |
| Manganese sulfate . 4H$_2$O | 7 | mg |
| Zinc sulfate . 7 H$_2$O | 3 | mg |
| Potassium iodide | 0.75 | mg |
| Boric acid | 1.5 | mg |

The extracts obtained by immersing the calli in methanol were concentrated and the resulting concentrates were fractionated into water layer (A) and ethylacetate layer (B) after additions of water and ethylacetate to the concentrates. To water layer (A) was added water-saturated n-butanol to effect fractionation into water layer and butanol layer. The n-butanol layer was concentrated and the concentrate was fractionated by silica-gel column chromatography. Thereafter the fractionate was concentrated and crystallized thrice with small amounts of water to yield 150 mg of yellow needle crystals.

The properties of the product agreed with those of the novel compound, i.e. echinatin-4-glucoside, which was synthesized, in Example 2. 750 mg of yellow echinatin crystals, melting point 210°–212° C, were obtained by fractionating the concentrates obtained from layer (B) and repeating crystallization thrice from a water-methanol system solvent. The water solubility of the echinatin at 15° C was not higher than 0.0001%.

EXAMPLE 7

50 l of a modified Murashige-Skoog's medium, prepared by adding 0.1 ppm indole-3-acetic acid, 5 ppm kinetin, 0.1 w/v% corn steep liquor and 2 w/v% maltose to a Murashige-Skoog's medium comprising the followings, was placed in a jar fermentor, inoculated with calli described in Example 6, and subjected to cultivation in a light place at a temperature of 27° C for 2 weeks.

| Murashige — Skoog's medium, per liter deionized water | | |
|---|---|---|
| Ammonium nitrate | 1650 | mg |
| Potassium nitrate | 1900 | mg |
| Potassium chloride . 2H$_2$O | 440 | mg |
| Magnesium sulfate . 7 H$_2$O | 370 | mg |
| Potassium dihydrogen phosphate | 170 | mg |
| Ferrous sulfate . 7 H$_2$O | 27.8 | mg |
| Sodium ethylenediaminetetraacetate | 37.3 | mg |
| Manganese sulfate . 4 H$_2$O | 22.3 | mg |
| Zinc sulfate . 7 H$_2$O | 8.6 | mg |
| Cobalt chloride . 6 H$_2$O | 0.025 | mg |
| Cupric sulfate . 5 H$_2$O | 0.025 | mg |
| Sodium molybdate . 2 H$_2$O | 0.25 | mg |
| Potassium iodide | 0.83 | mg |
| Boric acid | 6.2 | mg |

The culture broth was separated into calli (C) and filtrate (D) by filtration. Calli (C) was treated similarly as in Example 6 to yield 83 mg of echinatin-4-glucoside which showed properties identical to those of the product in said Example, and treating filtrate (D), similarly, as in Example 6 layer (A) yielded 112 mg of echinatin-4-glucoside which showed properties identical to those of the product in said Example.

Utility Example

The inhibiting action of echinatin-4'-glucoside on the growth of human lymphoblastoid.

Human lymphoblastoid cells (E. B.-3 cells, Burkitt lymphoma) were grown in suspension culture and maintained in 2 ml R.P.M.I. 1640 medium (manufactured by Flow Laboratories Inc., U.S.A.) supplemented with 30% fetal calf serum, placed in Petri's dish, diameter 20 mm at a temperature of 37° C.

On the fourth day after commencing the cultivation, 100 μg of echinatin-4'-glucoside per ml medium was added to the culture broth, and the resultant was compared with echinatin-4'-glucoside non-added culture broth on the inhibiting action on the growth of human lymphoblastoid cells.

The numbers of human lymphoblastoid cells were counted according to the method used for counting the numbers of leucocyte with Burke's blood count platelet.

As evident from the results illustrated in the Figure, echinatin-4'-glucoside possesses an inhibiting action on the growth of human lymphoblastoid cells.
What is claimed is:
1. Echinatin-4'-glucoside, represented by the formula
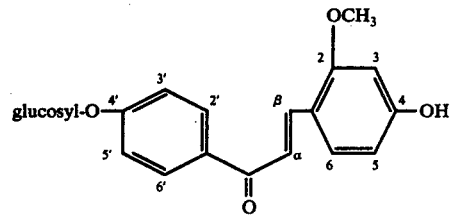
* * * * *